(12) United States Patent
Yamashita et al.

(10) Patent No.: US 7,074,581 B2
(45) Date of Patent: Jul. 11, 2006

(54) REAGENT FOR ASSAYING LIPID

(75) Inventors: Kazuaki Yamashita, Kobe (JP); Yasushi Shirahase, Kobe (JP)

(73) Assignee: Sysmex Corporation, Hyogo (JP)

( * ) Notice: Subject to any disclaimer, the term of this patent is extended or adjusted under 35 U.S.C. 154(b) by 378 days.

(21) Appl. No.: 10/633,518

(22) Filed: Aug. 5, 2003

(65) Prior Publication Data
US 2004/0067545 A1 Apr. 8, 2004

(30) Foreign Application Priority Data
Aug. 9, 2002 (JP) .............................. 2002-232695

(51) Int. Cl.
*C12Q 1/60* (2006.01)
(52) U.S. Cl. ............................ 435/11; 435/19; 435/188
(58) Field of Classification Search .................. 435/11, 435/19, 25, 188; 436/71
See application file for complete search history.

(56) References Cited

U.S. PATENT DOCUMENTS

| 4,275,154 A | * | 6/1981 | Hall ............................ 435/32 |
| 2003/0017523 A1 | * | 1/2003 | Hotta et al. .................... 435/25 |
| 2005/0027060 A1 | * | 2/2005 | Yagi et al. .................... 524/493 |
| 2005/0032141 A1 | * | 2/2005 | DiMagno et al. ............. 435/11 |

FOREIGN PATENT DOCUMENTS

JP 1 046 716 A1 * 10/2000

* cited by examiner

*Primary Examiner*—Ralph Gitomer
(74) *Attorney, Agent, or Firm*—Sughrue Mion, PLLC

(57) ABSTRACT

Effective stabilizing amount at least of one antioxidant is added to a composition containing an esterase and surfactant(s).

17 Claims, No Drawings

REAGENT FOR ASSAYING LIPID

This application claims priority to Japanese application JP2002/232695 filed Aug. 9, 2002.

BACKGROUND OF THE INVENTION

1. Field of the Invention

The present invention relates to reagents for assaying lipids containing an esterase, more particularly, to reagents for assaying neutral fats, total cholesterols, high-density lipoprotein cholesterols, and/or low-density lipoprotein cholesterols that can be used in the field of clinical chemistry.

2. Description of the Related Arts

'Esterase' is the generic name for enzymes that hydrolyzes esters among hydrolases, is classified in the group EC3.1, and includes lipases and cholesterol esterases. 'Lipase' is an enzyme that is also called 'glycerol ester hydrolase', hydrolyzes glycerol esters, and releases fatty acids, and includes many lipases having different substrate-specificities and localizations such as pancreatic lipase, lipoprotein lipase (LPL), hepatic triacyl glycerol lipase (HTGL), phospholipase, glycolipid-degrading lipase, sphingolipid-degrading lipase, and hormone-sensitive lipase.

Esterase is widely used for assaying lipid components such as neutral fats, cholesterol, phospholipids, glycolipids, sphingolipids, and lipoproteins in a specimen in the field of clinical test that covers assaying specific component(s) in a biological specimen.

Reagents that permit accurate and precise measurements are required in the field of clinical test. One of factors that disturb the accurate assay is the turbidity of biological specimens. The main reason for the turbidity of biological specimens is often chylomicron and ultra low-density lipoprotein that are lipoproteins. These lipoproteins contain neutral fats that are non-polar lipids at high levels, so that they often give turbidity in an aqueous solution. A method was disclosed in which a lipase is added to the reagent in order to solubilize the lipoprotein and to avoid its influence (Patent reference 1). As methods for avoiding the influence of the turbidity of a specimen, techniques that permit solubilizing, by various surfactants, the lipoprotein that causes the turbidity, have also been disclosed (Patent references 2–4). Since a method in which a lipase is added to a reagent cannot be used for a method for assaying lipoprotein(s) and/or lipid component(s) in which a lipase is used as a reactive component, a method in which a surfactant is added is used.

Another factor that prevents the accurate analysis is the stability of reagents. Many reagents that are used for the clinical test are provided as liquids or a lyophilized state. A lyophilized reagent is dissolved in a predetermined solution before use. After measurement, the remaining reagent is stored at a cool place until the next use. Therefore, the stability of a reagent and a liquid product until delivered for the use and/or during storage, and/or the stability of the solution when used, must be adequately secured. It is well known, however, that enzymes such as esterase are unstable in general. Under the present situation, this problem is dealt with by shortening the expiration date for use of a liquid product or a solution prepared by dissolving a lyophilized preparation, or by adding stabilizer(s). For example, when an esterase is used as a reagent, a surfactant that is expected to have a stabilizing effect may be used. It is believed that an esterase requires an interface (between water and oil) as a place for reacting with a lipid, so that surfactant(s) is/are often added to a reagent containing the esterase in order to create such a place to enhance the enzymatic activity of the lipase.

| | |
|---|---|
| Patent reference 1 | Japan Patent Laid-Open Pub. No. Hei 09-288111 |
| Patent reference 2 | Japan Patent Laid-Open Pub. No. Sho 59-162454 |
| Patent reference 3 | Japan Patent Laid-Open Pub. No. Sho 61-95247 |
| Patent reference 4 | Japan Patent Laid-Open Pub. No. 2001-188065 |

SUMMARY OF THE INVENTION

In such a situation, a phenomenon was observed that an esterase activity was remarkably reduced in a reagent containing an esterase and surfactant(s). The object of the present invention is to provide reagents solved the phenomenon.

As a result of zealous research by the applicants, it was found that the reason why an esterase activity is remarkable reduced in a reagent containing an esterase and a surfactant, is an oxidant formed by the oxidation of the surfactant. Under these finding, it was invented that the decrease in the stability of an esterase in a reagent containing a surfactant for assaying a lipid can be avoided by suppressing the action and/or the formation of an oxidant formed by the oxidation of the surfactant or by using a specific surfactant that is hardly oxidized, and the present invention has been achieved.

Thus, the present invention provides:
1. A reagent for assaying lipid comprising an esterase, a surfactant and an antioxidant.
2. The reagent according to item 1, wherein the esterase is a lipase and/or a cholesterol esterase.
3. The reagent according to item 2, wherein the lipase is at least one selected from a group consisting of lipoprotein lipase, phospholipase, pancreatic lipase, hepatic triacylglycerol lipase, glycolipid-degrading lipase, sphingolipid-degrading lipase and hormone-sensitive lipase.
4. The reagent according to item 1, wherein the surfactant is at least one selected from a group consisting of a nonionic surfactant, an anionic surfactant, a cationic surfactant and an amphoteric surfactant.
5. The reagent according to item 1, wherein the surfactant is a surfactant having polyoxyethylene group.
6. The reagent according to item 5, wherein the surfactant is at least one selected from a group consisting of polyoxyethylene isooctylphenyl ether, polyoxyethylene secondary alkyl ether, and polyoxyethylene octylphenyl ether.
7. The reagent according to item 1, wherein the antioxidant is at least one selected from a group consisting of butyl hydroxytoluene (BHT), α-tocopherol, β-thioglycol, methionine, vitamin C, ubiquinol, uric acid, bilirubin, glutathione, pyrroloquinoline quinone, carotenoid, probucol, polyphenol, butyl hydroxyanisole, thiotaurine, gallic acid, transferrin and phytic acid.
8. The reagent according to item 1, wherein the antioxidant is present at 1–100 mM.
9. The reagent according to item 1, wherein the antioxidant is present at 1–10 mM.
10. The reagent according to item 1, wherein the reagent for assaying lipid is reagent for assaying neutral fat (neutral fat assaying reagent).
11. The reagent according to item 10, wherein the natural fat assaying reagent comprises a first reagent and a second reagent, the first reagent comprising ATP, glucose-6- phosphate dehydrogenase and glycerol kinase; and the second reagent comprising an esterase, surfactant, antioxidant, glucose, NAD(P) and an ADP-dependent hexokinase.

12. The reagent according to item 1, wherein the reagent for assaying lipid is reagent for assaying total cholesterol (total cholesterol assaying reagent).
13. The reagent according to item 12, wherein the total cholesterol assaying reagent comprises a first reagent and a second reagent, the first reagent comprising an esterase, surfactant, antioxidant and NAD(P); and the second reagent comprising a cholesterol dehydrogenase.
14. The reagent according to item 1, wherein the reagent for assaying lipid is reagent for assaying high-density lipoprotein cholesterol (high-density lipoprotein cholesterol assaying reagent).
15. The reagent according to item 14, wherein the high-density lipoprotein cholesterol assaying reagent comprises a first reagent and a second reagent, the first reagent comprising NAD(P); and the second reagent comprising an esterase, surfactant, antioxidant and a cholesterol dehydrogenase.
16. The reagent according to item 1, wherein the reagent for assaying lipids is reagent for assaying low-density lipoprotein cholesterol (low-density lipoprotein cholesterol assaying reagent).
17. The reagent according to item 16, wherein the low-density lipoprotein cholesterol assaying reagent comprises a first reagent and a second reagent, the first reagent comprising an esterase, surfactant, antioxidant, NAD(P), and an LDL reaction inhibitor; and the second reagent comprising a cholesterol dehydrogenase.
18. A reagent for assaying lipid comprising an esterase, a surfactant and an antioxidant, wherein the surfactant is surfactant that forms substantially no oxidant under an oxidative condition for the surfactant.
19. The reagent according to item 18, wherein the surfactant is polyoxyethylene isooctylphenyl ether and/or polyoxyethylene nonylphenyl ether.

DESCRIPTION OF THE PREFERRED EMBODIMENT

Although a reagent for assaying lipids according to the present invention is described in more detail below, these descriptions are given not to limit the scope of the present invention, but only to exemplify the present invention.

The present invention was constituted based on the finding that the decrease in the activity of an esterase in a reagent containing an esterase and a surfactant for assaying lipids is due to an oxidant formed by the oxidation of the surfactant. The oxidant in the present invention includes peroxide such as hydrogen peroxide, oxygen free radical, and superoxide anion.

It is believed that surfactants are easily oxidized in general. Some surfactants are actually easily oxidized, while others are not. In other words, all the surfactants are not easily oxidized. Moreover, although it is believed that enzymes are easily oxidized by oxidants, some enzymes are easily oxidized by oxidant(s) and others not. In addition, some surfactants have an ability of stabilizing an enzyme or protein. Therefore, it is not easy even for persons skilled in the art to find that the stability of an esterase in a solution containing a surfactant is decreased by oxidant(s) formed by the oxidation of the surfactant. This was found by the applicants for the first time.

Moreover, not only a surfactant but also a substance that is contained in a reagent containing an esterase for assaying lipids and can form oxidant(s) might affect the stability of the esterase. Even in such a case, however, the stability of the esterase can be enhanced according to the present invention.

Antioxidants are compounds having an activity of suppressing the action and/or formation of oxidant(s). Antioxidants include butyl hydroxytoluene (BHT), α-tocopherol, β-thiodiglycol, methionine, vitamin C (ascorbic acid), ubiquinol, uric acid, bilirubin, glutathione, pyrroloquinoline quinone (PQQ), carotenoid (e.g., β-carotene, lycopin), probucol, polyphenol (e.g., flavonoids such as catechin, rutin, and quercetin), butyl hydroxyanisole [BHA; an analogue of dibutyl hydroxytoluene (BHT)], thiotaurine, gallic acid, transferrin, and phytic acid, but not limited to these. Any compounds capable of suppressing the action and/or formation of oxidant(s) formed can be used. In addition, compounds having no action of inactivating or inhibiting an esterase are preferably used. Butyl hydroxytoluene (BHT), α-tocopherol, β-thiodiglycol, or methionine is preferably used. Such a compound can be obtained, for example, by selecting a compound that permits keeping a lipase activity after storage for several days after adding a test compound to a composition containing a surfactant and an esterase (see Example 4).

One or more selected from the above compounds; for example, the above antioxidants can be used in order to suppress the action and/or formation of oxidant(s). The concentration of an antioxidant may depend on the species of the compound to be used, the activity of suppressing the action and/or formation of oxidant(s) and the species and concentration of a substance that can form oxidant(s) (e.g., surfactant), and can be determined by a simple series of experiments. It is preferable, for example, that BHT, α-tocopherol, β-thiodiglycol, or methionine is added to give the final concentration of 1 mM–10 mM, 0.01% (w/v)–0.1% (w/v), 1 mM–100 mM, or 1 nM–100 mM, respectively, to a composition containing a lipase that was prepared to contain Triton X-100 (Rohm & Haas Co.) at the final concentration of 0.5% (w/v).

The action and/or formation of oxidant(s) can be suppressed not only by using compounds such as an antioxidant but also by using enzymes such as oxidases including glutathione peroxidase, superoxide dismutase, catalase, ascorbate peroxidase, NADH peroxidase, phospholipase-A2-glutathione peroxidase coupled system, alkyl hydroperoxidoreductase, and NADH oxidase.

Surfactants applicable to the present invention include nonionic surfactants [e.g., octyl glycoside, heptyl thioglycoside, decanoyl-N-methylglucamide, polyoxyethylene dodecyl ether, polyoxyethylene heptamethylhexyl ether, polyoxyethylene isooctylphenyl ether (Triton-X series), polyoxyethylene secondary alkyl ether, polyoxyethylene octylphenyl ether, polyoxyethylene fatty acid ester, sucrose fatty acid ester, polyoxyethylene sorbitol ester (Tween series)], anionic surfactants (e.g., sodium dodecylsulfate, sodium dodecylsulfonate, sodium dodecyl-N-sarcosinate, sodium cholate, sodium deoxycholate, and sodium taurodeoxycholate), cationic surfactants (e.g., cetyl trimethylammonium bromide, tetradecyl ammonium bromide, and dodecylpyridinium chloride), and amphoteric surfactants (e.g., 3-[(3-cholamidopropyl)dimethylammonio]-1-propanesulfonic acid (CHAPS), 3-[(3-cholamidopropyl)dimethylammonio]-2-hydroxy-1-propanesulfonic acid (CHAPSO), palmitoyllysolecithin, dodecyl-N-betaine, and dodecyl-β-alanine), but are not limited to these.

Some surfactants give substantially no oxidant even under an oxidative condition. Using such a compound that is hardly oxidized is also included in the scope of the stabilization method according to the present invention. The "oxidative condition" for a surfactant means a condition under which oxidation of the surfactant is initiated and progresses. The oxidative condition includes the condition under which a surfactant is stored in a non-sealed transparent vessel and affected by the light or heat for a long time (e.g., several days or more) and the condition under which a surfactant is stirred in a sealed transparent vessel under an atmosphere of oxygen in the presence of the light. To "give substantially no oxidant" means that the concentration of a hydrogen peroxide-like substance formed is too low to affect the lipase activity, for example, that the concentration of a hydrogen peroxide-like substance formed by the oxidation under the above condition is about 5 μM or less. Such hardly oxidizable surfactants include Nonion NS-210 (polyoxyethylene nonylphenyl ether) and pure Triton X-100 (polyoxyethylene isooctylphenyl ether, Sigma Co., T-9284), but are not limited to these. Hardly oxidizable surfactants can be selected, for example, by storing an aqueous solution containing a surfactant under the light at room temperature, followed by assaying oxidant(s) formed (see Example 2). In addition, hardly oxidizable surfactants can be selected also by forcing the oxidation by stirring an aqueous solution containing a surfactant in a sealed transparent vessel under an atmosphere of oxygen in the presence of the light, followed by assaying oxidant(s) formed (see Example 3). When the term "Triton X-100" is used in the specification, the term does not mean "pure Triton X-100", but means one that can form a hydrogen peroxide-like substance under an oxidative condition.

Surfactants are added preferably at 0.001% (w/v)–10% (w/v), more preferably at 0.005% (w/v)–5% (w/v) for the present invention. These surfactants can be used single or in a combination of two surfactants or more. Surfactants that do not inactivate or inhibit enzyme such as lipase are preferably used.

Esterases applicable to the present invention include lipases and cholesterol esterases. Such lipases include lipoprotein lipase (LPL), phospholipase, pancreatic lipase, hepatic triacyl glycerol lipase (HTGL), glycolipid-degrading lipase, sphingolipid-degrading lipase, and hormone-sensitive lipase. Preferable lipase is LPL. The lipases can be derived from animal or human serum, or ones prepared by the genetic engineering technique, and are not limited by the origin, the preparation method, or the state of existence. The concentration of the lipases can be adjusted to give an objective enzymatic activity.

A buffer solution is usually used for a liquid reagent containing an esterase for assaying lipids, wherein the buffer solution is prepared with buffer(s) having a buffer ability at pH4–9 with the buffer(s) being one of more selected from the group consisting of MES, HEPES, MOPS, BIS-TRIS, TRIS, MOPSO, and ADA. One or more preservative(s) selected from the group consisting of sodium azide, ciprofloxacin, propionic acid and sodium benzoate, can also be added. If necessary, salts such as sodium chloride and/or generally used stabilizers such as amino acids and saccharides, can also be added.

Thus obtained reagent containing an esterase for assaying lipids is more stable than the conventionally used reagent containing an esterase for assaying lipids, i.e., useful. More concretely, a surfactant such as Triton X-100 and an antioxidant such as BHT are added to 10 mM–1,000 mM buffer at a concentration of 0.01% (w/v)–10% (w/v) and 1 mM–10 mM, respectively. After a preservative is added, pH of the obtained solution is adjusted to 6–7 or so to give mother liquor. An esterase is added to this mother liquor at a predetermined concentration or activity to give a solution containing the esterase. The obtained solution can be filtrated with a filter having an appropriate pore size. Thus prepared esterase solution is provided as a liquid reagent or dry preparation after lyophilization. The above example is given to exemplify compositions according to the present invention, but not to limit the scope of the present invention.

The reagent containing an esterase for assaying lipids can be widely used as a reagent for assaying lipid components in specimen such as neutral fats, cholesterol, phospholipids, glycolipids, sphingolipids, and lipoproteins. Thus, the present invention can provide a reagent kit consisting of one container or more containing the above reagent for assaying lipids. The reagent (kit) for assaying lipids has an excellent stability as products and/or during storage, so that that reagent (kit) permits accurate and precise measurements that are the most important as an assay reagent.

Concrete reagents for assaying lipids include reagents for assaying neutral fats consisting of a first reagent containing ATP, a glucose-6-phosphate dehydrogenase and a glycerol kinase and a second reagent containing an esterase, surfactant(s), antioxidant(s), glucose, NAD(P) and ADP-dependent hexokinase, a total cholesterol assay reagent consisting of a first reagent containing an esterase, a surfactant, an antioxidant and NAD(P) and a second reagent containing cholesterol dehydrogenase, and reagents for assaying a low density lipoprotein cholesterol assay reagent consisting of a first reagent containing an esterase, surfactant(s), antioxidant(s), NAD(P) and LDL reaction inhibitor and a second reagent containing a cholesterol dehydrogenase.

Compounds inhibiting the reaction between the esterase and LDL can be used as LDL reaction inhibitors. Those compounds include a calix arene sulfate, sucrose, bovine serum albumin, calix arenes, polyanions, polyethyleneglycol and combinations of polyanions and divalent cations. The polyanions include polysaccharidesulfates such as dextransulfate and heparin, phosphotungstic acid, a salt thereof and poly(ethylene glycol). The divalent cations include $Mg^{2+}$, $Mn^{2+}$, $Ca^{2+}$, and $Ni^{2+}$.

The 'calix arenes' are cyclic oligomers obtained by cyclically polymerizing 4–8 molecules of phenol with methylene moiety, and include calix (4) arene, calix (6) arene, calix (8) arene, calix (4) arenesulfuric acid, calix (6) arenesulfuric acid, calix (8) arenesulfuric acid, calix (4) areneacetic acid, calix (6) areneacetic acid, calix (8) areneacetic acid, calix (4) arenecarboxylic acid, calix (6) arenecarboxylic acid, calix (8) arenecarboxylic acid, calix (4) areneamine, calix (6) areneamine, and calix (8) areneamine.

EXAMPLE 1

The stability of a lipoprotein lipase in the presence of nonionic surfactant Triton X-100 was comparatively tested with respect to Triton X-100 contained in a shaded, completely sealed container and Triton X-100 contained in a polyethylene container on a bench.

A reagent A for assay of neutral fats was prepared, by adding, if necessary, Triton X-100 (Rohm & Haas Co.) at 0.5% (w/v) to an aqueous solution (pH6.5) containing 50 mM MES, 100 mM oxalic acid, 80 mM glucose, 6.0 mM β-NADP, 0.1% sodium azide, 10.0 U/mL ADP-dependent hexokinase, and 1,500 U/mL of a lipoprotein lipase, and the obtained solution was stored at 37° C. for 6 days, and a lipase activity was assayed.

300 μl of the reagent B having the composition described below for assaying a lipase activity was added to 10 μl of a preparation prepared by ten folds diluting the above reagent A with a solution (pH 6.5) containing 50 mM MES and 0.1% BSA, and the obtained mixture was incubated at 37° C. for 5 min. Then 50 μl of the substrate having the composition described below for assaying a lipase was added. 2 min after the addition, a lipase activity was assayed by measuring the change in absorbance at a dominant wavelength of 340 nm and a subdominant wavelength of 600 nm.

| Reagent B for assaying lipase activity (pH 7.5) | |
|---|---|
| Bicine | 50.0 mM |
| HEPES | 23.3 mM |
| Potassium chloride | 100.0 mM |
| Magnesium chloride · 6H$_2$O | 8.1 mM |
| Glucose | 27.0 mM |
| Triton X-100 | 0.208% |
| ATT · 2Na | 2.7 mM |
| β-NADP (oxidized form) | 1.9 mM |
| Glycerol kinase | 2.3 U/mL |
| Glucose-6-phosphate dehydrogenase (G6PDH) | 4.3 U/mL |
| ADP-dependent hexokinase | 2.7 U/mL |
| Substrate for assaying lipase activity | |
| High-level check lipid* | Dissolved in 9.0 mL of purified water |

*A product of International Reagent Company (IRC) containing several kinds of highly concentrate lipid.

Remaining activities were determined with the lipase activity of the above solution stored at 2–8° C. being 100%, and were summarized in Table 1. The stability of a lipoprotein lipase was enhanced by the addition of Triton X-100 stored in a completely sealed container compared with no addition. It is clear that the surfactant per se has an effect of stabilizing the lipoprotein lipase. However, it was found, however, that the longer the storage period is, the more the stability of the lipoprotein lipase is decreased when Triton X-100 left on the bench in a polyethylene container was used.

TABLE 1

Effect of surfactant on stability of lipoprotein lipase (stored at 37° C.)

| Storage period | Remaining activity of lipase (%) |
|---|---|
| 12 months | 28.4 |
| 9 months | 32.4 |
| 6 months | 45.5 |
| 3 months | 55.6 |
| Stored in completely sealed container (12 months) | 82.5 |
| No addition (12 months) | 67.0 |

EXAMPLE 2

The stability of a lipoprotein lipase in the presence of each of various surfactants was determined. Samples were prepared using various surfactants in a manner similar to Example 1, and were stored at 30° C. for 6 days, and the remaining activity of the lipoprotein lipase was determined in a manner similar to Example 1, and the stabilities of the lipoprotein lipase were compared each other.

In addition, hydrogen peroxide-like substance in 5% (w/v) aqueous solution of each of various surfactants was assayed by the enzymatic colorimetry using a peroxidase derived from a bacterium as follows: 200 μl of the first reagent having the composition as described below was added to 20 μl of the sample, and the obtained mixture was incubated for reaction at 37° C. for 5 min, and then an absorbance at 600 nm was measured, and then 50 μl of the second reagent having the composition as described below was added to the resultant mixture, and the obtained mixture was further incubated fro reaction at 37° C. for 5 min, and the absorbance at 600 nm was measured, and hydrogen peroxide-like substance was assayed by the difference between absorbancies before and after addition of the second reagent.

| First Regent (pH 7.0) | |
|---|---|
| BES | 939 mg |
| Bis-Tris | 320 mg |
| HDAOS | 24 mg |
| Bovine serum albumin (BSA) | 200 mg |
| Total volume | 100 mL |

HADAOS is N-(2-hydroxy-3-sulfopropyl)-3,5-dimethoxyaniline sodium salt.

| Second Regent (pH 7.0) | |
|---|---|
| BES | 375.6 mg |
| Bis-Tris | 128.0 mg |
| 4-Aminoantipyrin | 130.4 mg |
| BSA | 80.0 mg |
| Peroxidase | 1500 U |
| Total volume | 40 mL |

Thirty per cent hydrogen peroxide (H$_2$O$_2$) was properly diluted with purified water and was used as standard solutions.

Results are summarized in Table 2. The more a surfactant to be added contains hydrogen peroxide-like substance, the more the stability of the lipoprotein lipase was decreased. Various contents of hydrogen peroxide-like substance were detected in surfactants stored under different situations for different periods. The remaining activity of lipoprotein lipase was negatively correlated with the content of hydrogen peroxide-like substance contained in the surfactant used.

TABLE 2

Correlation between decrease in stability of lipoprotein lipase and hydrogen peroxide-like substance in surfactant aqueous solution

| Surfactant | Remaining activity of lipase (%) | Hydrogen peroxide-like substance (μM) |
|---|---|---|
| Triton X-100 | 51.6 | 18.08 |
| Triton X-100 | 82.5 | 2.78 |
| NIKKOL OP-10 | 85.5 | 0.43 |
| NIKKOL BT-9 | 68.9 | 4.58 |
| NIKKOL BT-9 | 98.4 | 0.32 |
| Nonion NS-210 | 96.9 | 0.03 |
| Nonion HS-210 | 73.6 | 7.91 |
| Nonion HS-210 | 91.3 | 0.09 |
| Emulgen 810 | 91.5 | 0.13 |
| Emulgen 909 | 90.8 | 3.10 |
| Hydrogen peroxide aqueous solution | 26.9 | 34.45 |

Results of Example 1 and results of Example 2 suggested that hydrogen peroxide-like substance in the surfactant aqueous solution is related with the inactivation of lipoprotein lipase. It was considered that oxidant(s) formed by the oxidation of surfactants inactivate(s) the lipoprotein lipase.

EXAMPLE 3

The effect of surfactants that were forced to be oxidized on the lipase stability was studied in order to confirm that the inactivation of the lipoprotein lipase in a solution containing surfactant(s) is due to oxidant(s) formed by the oxidation of the surfactant.

10% (w/v) aqueous solutions containing each of Triton X-100 (Rohm & Haas Co.), pure Triton X-100 (Sigma Co., T-9284), and Nonion NS-210 were prepared, and were transferred into conical glass flasks, and each atmosphere was replaced with oxygen gas, and the flasks were plugged, and stirred in light in order to force to oxidize surfactant(s). Surfactant aqueous solutions that are not forced to be oxidized were transferred into conical glass flasks after preparation, and each atmosphere was replaced with argon gas, and the flasks were plugged, and stored in the dark. Samples were prepared, in a manner similar to Example 1, using the surfactant forced to be oxidized and the surfactant not forced to be oxidized, and incubated at 37° C. for 6 days, and a remaining lipoprotein lipase activity was assayed in a manner similar to Example 1 to compare the stability of the lipoprotein lipase. In addition, hydrogen peroxide-like substance(s) in a 10% (w/v) aqueous solution of each surfactant was/were assayed in a manner similar to Example 2.

As shown in Table 3, it was found that hydrogen peroxide-like substance(s) is/are formed by the oxidation of surfactant(s), that the stability of the lipoprotein lipase is remarkably decreased by a surfactant containing an enhanced concentration of hydrogen peroxide-like substance(s) by the oxidation of surfactant(s), and that Nonion NS-210 and pure Triton X-100 give only a small amount of hydrogen peroxide-like substance even by the forced oxidation, so that the stability of the lipoprotein lipase is not affected.

These results elucidated that oxidant(s) formed by the oxidation of surfactant(s) decrease(s) the stability of the lipoprotein lipase, and that using surfactant(s) that give(s) substantially no oxidant even under an oxidative condition permits keeping the stability of the lipoprotein lipase.

TABLE 3

Decrease in stability of lipoprotein lipase by oxidation of surfactant

| Surfactant | Forced oxidation | Remaining lipase Activity (%) | Hydrogen peroxide-like substance (μM) |
|---|---|---|---|
| Triton X-100 | Conducted | 65.4 | 15.63 |
|  | No | 80.5 | 8.16 |
| Triton X-100 (Pure) | Conducted | 82.0 | 0.50 |
|  | No | 85.6 | 0.28 |
| Nonion NS-210 | Conducted | 89.6 | 0.10 |
|  | No | 89.9 | 0.08 |

EXAMPLE 4

Effect of reach of various compounds on the decrease in the stability of a lipoprotein lipase in a solution containing a surfactant was studied. 0.5% (w/v) Triton X-100 (Rohm & Haas Co.) was used as the surfactant, and each of various compounds was added to the sample prepared in a manner similar to Example 1, and the obtained mixtures were incubated at 37° C. for 6 days, and remaining lipoprotein lipase activities were determined in a manner similar to Example 1 to compare the stabilities of the lipoprotein lipase each other.

It was confirmed that the lipoprotein lipase is stabilized by an antioxidant such as butyl hydroxytoluene (BHT), α-tocopherol, β-thiodiglycol, and methionine in a solution containing a surfactant.

TABLE 4

Enhancement of stability of lipoprotein lipase by addition of antioxidant (stored at 37° C.)

| Compound name | Concentration | Remaining lipase activity (%) |
|---|---|---|
| BHT | 5 mM | 84.1 |
| α-Tocopherol | 0.05% | 80.2 |
| β-Thiodiglycol | 0.5% | 93.7 |
| L-Methionine | 10 mM | 94.4 |
| EDTA · 2Na | 5 mM | 41.6 |
| BSA | 0.5% | 61.4 |
| Sucrose | 1.0% | 42.3 |
| Trehalose | 1.0% | 42.8 |
| HB · β · CD | 1.0% | 43.9 |
| No addition | — | 44.3 |

As a summary of the above results, compositions of reagents, for assaying neutral fats and total cholesterols, which enhanced the stability of esterase(s), are given below:

Reagents for assaying neutral fats: The first regent is an aqueous solution (pH8.0) containing 50 mM HEPES, 10 mM magnesium chloride, 3.5% Nonion A-10R, 1.2% Triton X-100, 3 mM phosphoenolpyruvic acid, 3 mM ATP, 4 U/mL, G6PDH, 3 U/mL pyruvate kinase and 1.5 U/mL glycerol kinase; The second regent is an aqueous solution (pH 6.5) containing 50 mM MES, 100 mM oxalic acid, 80 mM glucose, 6.0 mM β-NADP, 0.1% sodium azide, 10 U/mL ADP-dependent hexokinase, 1,500 U/mL lipoprotein lipase, 0.5% (w/v) Triton X-100 (Rohm & Haas Co.), and 5 mM BHT Regents for assaying total cholesterols: The first reagent is an aqueous solution (pH 7.0) containing 25 mM PIPES, 100 mM hydrazinium dichloride, 3% Nonion A-10R, 4% Triton X-100, 20 mM sodium cholate, 6.0 mM β-NAD, 2.5 U/mL cholesterol esterase, and 5 mM BHT; The second reagent is an aqueous solution (pH 8.5) containing 50 mM TAPSHEPES, 5 mM sodium cholate, 14 U/mL cholesterol dehydrogenase (pH 8.5).

These compositions are summarized in the following tables.

TABLE 5

Compositions of reagents for assaying neutral fats

| First Regent | | Second Regent | |
|---|---|---|---|
| Composition | Concentration | Composition | Concentration |
| HEPES | 50 mM | MES | 50 mM |
| Magnesium chloride | 10 mM | Oxalic acid | 100 mM |
| Nonion A-10R | 3.5% | Glucose | 80 mM |
| Triton X-100 | 1.20% | β-NADP | 6 mM |
| Phosphoenol-pyruvic acid | 3 mM | Sodium azide | 0.1% |
| ATP | 3 mM | ADP-dependent hexokinase | 10 U/mL |
| G6PDH | 4 U/mL | Lipoprotein lipase | 1,500 U/mL |
| Pyruvate kinase | 3 U/mL | Triton X-100 | 0.5% |

TABLE 5-continued

Compositions of reagents for assaying neutral fats

| First Regent | | Second Regent | |
|---|---|---|---|
| Composition | Concentration | Composition | Concentration |
| Glycerokinase (pH 8.0) | 1.5 U/mL | BHT (pH 6.5) | 5 mM |

TABLE 6

Compositions of reagents for assaying total cholesterols

| First Regent | | Second Regent | |
|---|---|---|---|
| Composition | Concentration | Composition | Concentration |
| PIPES | 25 Mm | TAPS | 50 mM |
| Hydrazinium dichloride | 100 mM | Sodium cholate | 5 mM |
| Nonion A-10R | 3% | Cholesterol dehydrogenase (pH 8.5) | 14 U/mL |
| Triton X-100 | 4% | | |
| Sodium cholate | 20 mM | | |
| β-NAD | 6 mM | | |
| Cholesterol esterase | 2.5 U/mL | | |
| BHT (pH 7.0) | 5 mM | | |

INDUSTRIAL USEFULNESS

As set forth hereinabove, a reagent for assaying lipids according to the present invention permits providing a reagent composition for clinical test that can be stored for a long period and permits accurate assay, i.e., is very useful.

NAD(P) means an equilibrium state between NAD and NAPD, i.e., both NAD and NAD(P) are present.

Variations of the invention will be apparent to the skilled artisan.

What is claimed is:

1. A reagent for assaying lipid comprising an esterase, a surfactant and an antioxidant selected from the group consisting of thiodiglycol and methionine.

2. The reagent according to claim 1, wherein the esterase is at least one esterase selected from the group consisting of a lipase and a cholesterol esterase.

3. The reagent according to claim 2, wherein the lipase is at least one lipase selected from the group consisting of lipoprotein lipase, phospholipase, pancreatic lipase, hepatic triacylglycerol lipase, glycolipid-degrading lipase, sphingolipid-degrading lipase and hormone-sensitive lipase.

4. The reagent according to claim 1, wherein the surfactant is at least one surfactant selected from the group consisting of a nonionic surfactant, an anionic surfactant, a cationic surfactant and an amphoteric surfactant.

5. The reagent according to claim 1, wherein the surfactant is a surfactant having a polyoxyethylene group.

6. The reagent according to claim 5, wherein the surfactant is at least one surfactant selected from the group consisting of polyoxyethylene isooctyiphenyl ether, polyoxyethylene secondary alkyl ether, and polyoxyethylene octylphenyl ether.

7. The reagent according to claim 1, wherein the antioxidant is present at a concentration of 1–100 mM.

8. The reagent according to claim 1, wherein the antioxidant is present at a concentration of 1–10 mM.

9. The reagent according to claim 1, wherein the reagent is used for assaying neutral fat.

10. The reagent according to claim 9, wherein the reagent for assaying neutral fat comprises a first reagent composition and a second reagent composition, the first reagent composition comprising ATP, glucose-6-phosphate dehydrogenase and glycerol kinase; and the second reagent composition comprising an esterase, a surfactant, an antioxidant, glucose, NAD(P) and an ADP-dependent hexokinase.

11. The reagent according to claim 1, wherein the reagent is used for assaying total cholesterol.

12. The reagent according to claim 11, wherein the reagent for assaying total cholesterol comprises a first reagent composition and a second reagent composition, the first reagent composition comprising an esterase, a surfactant, an antioxidant and NAD(P); and the second reagent composition comprising a cholesterol dehydrogenase.

13. The reagent according to claim 1, wherein the reagent is used for assaying high-density lipoprotein cholesterol.

14. The reagent according to claim 13, wherein the reagent for assaying high-density lipoprotein cholesterol comprises a first reagent composition and a second reagent composition, the first reagent composition comprising NAD (P); and the second reagent composition comprising an esterase, a surfactant, an antioxidant and a cholesterol dehydrogenase.

15. The reagent according to claim 1, wherein the reagent is used for assaying low-density lipoprotein cholesterol.

16. The reagent according to claim 15, wherein the reagent for assaying low-density lipoprotein cholesterol (LDL) comprises a first reagent composition and a second reagent composition, the first reagent composition comprising an esterase, a surfactant, an antioxidant, NAD(P), and compounds inhibiting the reaction between the esterase and LDL; and the second reagent composition comprising a cholesterol dehydrogenase.

17. The reagent according to claim 16, wherein said compounds inhibiting the reaction between the esterase and LDL are selected from the group consisting of a calix arene sulfate, sucrose, bovine serum albumin, calix arenes, polyanions, polyethylene glycol and combinations of polyanions and divalent cations.

* * * * *